US009933387B1

(12) United States Patent
McCanna et al.

(10) Patent No.: US 9,933,387 B1
(45) Date of Patent: Apr. 3, 2018

(54) MINIATURIZED SUB-NANOAMPERE SENSITIVITY LOW-NOISE POTENTIOSTAT SYSTEM

(71) Applicant: Biolinq, Inc., La Jolla, CA (US)

(72) Inventors: James McCanna, San Diego, CA (US); Joshua Windmiller, Del Mar, CA (US)

(73) Assignee: Biolinq, Inc., San Diego, CA (US)

( * ) Notice: Subject to any disclaimer, the term of this patent is extended or adjusted under 35 U.S.C. 154(b) by 406 days.

(21) Appl. No.: 14/843,926

(22) Filed: Sep. 2, 2015

Related U.S. Application Data

(60) Provisional application No. 62/046,996, filed on Sep. 7, 2014.

(51) Int. Cl.
*G01N 27/327* (2006.01)

(52) U.S. Cl.
CPC .............................. *G01N 27/3273* (2013.01)

(58) Field of Classification Search
CPC .................................................. G01N 27/3273
See application file for complete search history.

(56) References Cited

U.S. PATENT DOCUMENTS

| | | | |
|---|---|---|---|
| 4,305,401 A | 12/1981 | Reissmueller et al. |
| 4,323,996 A | 4/1982 | Ganter |
| 4,407,295 A | 10/1983 | Steuer et al. |
| 5,131,390 A | 7/1992 | Sakaguchi et al. |
| 5,279,543 A | 1/1994 | Glikfeld et al. |
| 5,286,364 A | 2/1994 | Yacynych et al. |
| 5,540,828 A | 7/1996 | Yacynych |
| 5,730,714 A | 3/1998 | Guy et al. |
| 5,766,132 A | 6/1998 | Yasukawa et al. |
| 5,832,410 A * | 11/1998 | Lin .................... G01N 27/3273 204/400 |
| 6,036,055 A | 3/2000 | Mogadam et al. |
| 6,132,449 A | 10/2000 | Lum et al. |
| 6,139,718 A | 10/2000 | Kurnik et al. |
| 6,269,053 B1 | 7/2001 | Kawata et al. |
| 6,284,126 B1 | 9/2001 | Kurnik et al. |
| 6,364,890 B1 | 4/2002 | Lum et al. |
| 6,413,396 B1 | 7/2002 | Yang et al. |
| 6,471,903 B2 | 10/2002 | Sherman et al. |
| 6,603,987 B2 | 8/2003 | Whitson |

(Continued)

FOREIGN PATENT DOCUMENTS

| WO | WO2009034313 | 3/2009 |
|---|---|---|
| WO | WO2009064164 | 5/2009 |

(Continued)

OTHER PUBLICATIONS

Windmiller, et al. "Bioelectronic system for the control and readout of enzyme logic gates" Sensors and Actuators B: Chemical, vol. 155, No. 1, Jul. (Year: 2011).*

(Continued)

*Primary Examiner* — J. Christopher Ball
(74) *Attorney, Agent, or Firm* — Clause Eight IPS; Michael Catania

(57) ABSTRACT

A miniaturized sub-nanoampere sensitivity low-noise potentiostat system is disclosed herein. The system includes an adjustable bias analog front end/potentiostat, a plurality of high input impedance and high gain difference amplifiers, means for signal filtering, a high-resolution analog-to-digital converter, and a sampling algorithm.

9 Claims, 11 Drawing Sheets

(56) References Cited

U.S. PATENT DOCUMENTS

| | | |
|---|---|---|
| 6,814,845 B2 | 11/2004 | Wilson et al. |
| 6,862,466 B2 | 3/2005 | Ackerman |
| 6,908,453 B2 | 6/2005 | Fleming et al. |
| 7,097,776 B2 | 8/2006 | Raju |
| 7,132,054 B1 | 11/2006 | Kravitz et al. |
| 7,262,068 B2 | 8/2007 | Roy et al. |
| 7,343,188 B2 | 3/2008 | Sohrab |
| 7,344,499 B1 | 3/2008 | Prausnitz et al. |
| 7,415,299 B2 | 8/2008 | Zimmermann et al. |
| 7,429,333 B2 | 9/2008 | Chiou et al. |
| 7,456,112 B2 | 11/2008 | Lee |
| 7,473,244 B2 | 1/2009 | Frazier et al. |
| 7,493,232 B1 | 2/2009 | Surina |
| 7,837,654 B2 | 11/2010 | Shumate et al. |
| 7,949,382 B2 | 5/2011 | Jina |
| 8,022,292 B2 | 9/2011 | Arianpour et al. |
| 8,088,321 B2 | 1/2012 | Ferguson et al. |
| 8,108,023 B2 | 1/2012 | Mir et al. |
| 8,160,665 B2 | 4/2012 | Mischler et al. |
| 8,280,476 B2 | 10/2012 | Jina |
| 8,574,165 B2 | 11/2013 | Marsh |
| 8,798,799 B2 | 8/2014 | Deo et al. |
| 9,387,000 B2 | 7/2016 | Corrie et al. |
| 9,551,698 B2 | 1/2017 | Huys et al. |
| 2003/0225360 A1 | 12/2003 | Eppstein et al. |
| 2006/0015061 A1 | 1/2006 | Kuo et al. |
| 2006/0264716 A1 | 11/2006 | Zander |
| 2007/0170054 A2 | 7/2007 | Wilsey |
| 2007/0213044 A1 | 9/2007 | Steingart et al. |
| 2007/0282246 A1 | 12/2007 | Henley |
| 2008/0097352 A1 | 4/2008 | Beck et al. |
| 2008/0154107 A1 | 6/2008 | Jina |
| 2008/0234562 A1 | 9/2008 | Jina |
| 2009/0069651 A1 | 3/2009 | Zimmermann et al. |
| 2009/0069697 A1 | 3/2009 | Frazier et al. |
| 2009/0088652 A1 | 4/2009 | Tremblay |
| 2009/0131778 A1 | 5/2009 | Jina et al. |
| 2009/0143761 A1 | 6/2009 | Cantor et al. |
| 2009/0259118 A1 | 10/2009 | Feldman et al. |
| 2010/0049021 A1 | 2/2010 | Jina et al. |
| 2010/0286803 A1 | 11/2010 | Tillotson |
| 2011/0105871 A1 | 5/2011 | Zimmermann et al. |
| 2011/0237925 A1 | 9/2011 | Yue et al. |
| 2012/0172692 A1 | 7/2012 | Tamada et al. |
| 2012/0323097 A9 | 12/2012 | Chowdhury |
| 2013/0053660 A1 | 2/2013 | Shieh |
| 2013/0065257 A1 | 3/2013 | Wang et al. |
| 2013/0144131 A1 | 6/2013 | Wang et al. |
| 2013/0225956 A1 | 8/2013 | Huang et al. |
| 2013/0281808 A1 | 10/2013 | Shieh |
| 2014/0259652 A1 | 9/2014 | Pushpala et al. |
| 2014/0275897 A1 | 9/2014 | Pushpala et al. |
| 2014/0336487 A1 | 11/2014 | Wang et al. |
| 2015/0276758 A1 | 10/2015 | Addisu |
| 2015/0313527 A1 | 11/2015 | Renlund |
| 2016/0029937 A1 | 2/2016 | Sia et al. |
| 2016/0058342 A1 | 3/2016 | Maiz-Aquinaga et al. |
| 2016/0095541 A1 | 4/2016 | Wang et al. |
| 2016/0296149 A1 | 10/2016 | Polsky et al. |
| 2016/0302687 A1 | 10/2016 | Lee et al. |
| 2017/0007813 A1 | 1/2017 | Negi et al. |

FOREIGN PATENT DOCUMENTS

| | | |
|---|---|---|
| WO | WO2010120364 | 10/2010 |
| WO | WO2012020332 | 2/2012 |
| WO | WO2013058879 | 4/2013 |

OTHER PUBLICATIONS

Data sheet for a LMP2234 quad micropower precision amplifier, Texas Instruments, Sep. 2007, rev Mar. 2013. (Year: 2013).*

* cited by examiner

MINIATURIZED SUB-NANOAMPERE SENSITIVITY LOW-NOISE POTENTIOSTAT SYSTEM

CROSS REFERENCE TO RELATED APPLICATION

The Present Application claims priority to U.S. Provisional Patent Application No. 62/046,996, filed on Sep. 7, 2014, which is hereby incorporated by reference in its entirety.

STATEMENT REGARDING FEDERALLY SPONSORED RESEARCH OR DEVELOPMENT

Not Applicable

BACKGROUND OF THE INVENTION

Field of the Invention

The present invention generally relates to a potentiostat system. More specifically, a system enabling the electrochemical detection of low concentrations of analytes.

Description of the Related Art

The prior art discusses various techniques for amperometry and voltammetry.

Amperometry and voltammetry are common analytical techniques employed in electrochemistry to ascertain the concentration of a target analyte. Such measurements are routinely performed utilizing an instrument known as a potentiostat, which serves to either apply a fixed potential (amperometry) or time-varying potential (voltammetry) while subsequently measuring the magnitude of the electric current flowing through an electrochemical cell (or sensor) in response to this applied voltage stimulus. Common potentiostat devices are capable of reading current in the range of one microampere to ten milliamperes, limiting their ability to detect extremely low levels of analytes. Some benchtop laboratory devices can achieve nanoampere-level sensitivity but require specialized components to ensure correct readings. Nanoamp sensitivity facilitates the electrochemical detection of very low concentrations of analytes; this is of fundamental importance when attempting detection in unprocessed samples where target analytes, such as biomarkers in physiological fluids or trace contaminants in environmental samples, may be found at very low concentrations (parts-per-billion or parts-per-trillion). Laboratory devices with high precision cost above $10,000 USD and require large housings to shield internal components, limiting their practical applications and usage outside of stationary central locations and hence are not amenable to home- or field-based use.

Conductometry is a measurement of electrical conductivity to monitor progress of chemical reaction.

Voltammetry is the study of redox current g as a function of applied potential in an electrochemical cell. Polography is a subclass of voltammetry using electrodes with broad cathodic ranges.

Amperometry refers to the detection of analytes in a solution at a defined potential based on electric ent or changes in electric current arising from a redox reaction involving the said analyte.

BRIEF SUMMARY OF THE INVENTION

The present invention solves the problem of the inability to measure nanoampere-level (or lower) currents without the use of external shielding elements and high cost, high precision electronic components housed in a stationary benchtop analyzer.

One aspect of the present invention is a cascade of a set of low cost, high impedance components & integrated circuits that provide high precision, high gain, and noise reduction for sub-nanoamp detection sensitivity.

Another aspect of the present invention is a miniaturized sub-nanoampere sensitivity low-noise potentiostat system. The system comprises an adjustable bias analog front end/potentiostat, an adjustable low noise transimpedance amplifier, a mirrored (inverted input) high input impedance and high (adjustable) gain difference amplifier, means for signal filtering, a high-resolution analog-to-digital converter, and a sampling algorithm.

Yet another aspect of the present invention is a scalable linear-output potentiostat system for the detection of extremely low currents. The system includes a high precision and high input impedance analog front end, a high precision integrator, and a plurality of high input impedance and high gain difference amplifiers.

Yet another aspect of the present invention is a system for measuring the magnitude of an electric current flowing through an electrochemical cell. The system includes an adjustable bias analog front end/potentiostat, an adjustable low noise transimpedance amplifier, a mirrored (inverted input) high input impedance and high (adjustable) gain difference amplifier, means for signal filtering, a high-resolution analog-to-digital converter, and a sampling algorithm.

Yet another aspect of the present invention is system for electrochemical detection of low concentrations of analytes. The system includes a high precision and high input impedance analog front end, a high precision integrator, and a plurality of high input impedance and high gain difference amplifiers.

Yet another aspect of the present invention is system for detection of extremely low currents. The system includes a high precision and high input impedance analog front end, a high precision integrator, and a plurality of high input impedance and high gain difference amplifiers.

Yet another aspect of the present invention is system for measuring nanoampere currents. The system includes a high precision and high input impedance analog front end, a high precision integrator, and a plurality of high input impedance and high gain difference amplifiers.

Yet another aspect of the present invention is a miniaturized sub-nanoampere sensitivity low-noise potentiostat system. The system includes an adjustable bias analog front end/potentiostat, a plurality of high input impedance and high gain difference amplifiers, means for signal filtering, a high-resolution analog-to-digital converter, and a sampling algorithm.

Yet another aspect of the present invention is a system for measuring the magnitude of an electric current flowing through an electrochemical cell. The system includes an adjustable bias analog front end/potentiostat, a plurality of high input impedance and high gain difference amplifiers, means for signal filtering, a high-resolution analog-to-digital converter, and a sampling algorithm.

Preferably, the filtering means comprises at least one of an active filter, a passive filter, a low pass filter, a high pass filter or a band pass filter.

Alternatively, the filtering means comprises a combination of at least two of a high pass filter, a band pass filter, a passive low pass filter, and an active filter.

Yet another aspect of the present invention is as a system for coulometry. The system includes a high precision and high input impedance analog front end, a high precision integrator, and a plurality of high input impedance and high gain difference amplifiers.

Yet another aspect of the present invention is as a system for polarography. The system includes a high precision and high input impedance analog front end, a high precision integrator, and a plurality of high input impedance and high gain difference amplifiers.

Yet another aspect of the present invention is as a system for conductometry. The system includes a high precision and high input impedance analog front end, a high precision integrator, and a plurality of high input impedance and high gain difference amplifiers.

Yet another aspect of the present invention is as a system for impedimetry. The system includes a high precision and high input impedance analog front end, a high precision integrator, and a plurality of high input impedance and high gain difference amplifiers.

Yet another aspect of the present invention is as a system for amperometry. The system includes a high precision and high input impedance analog front end, a high precision integrator, and a plurality of high input impedance and high gain difference amplifiers.

Yet another aspect of the present invention is as a system for voltammetry. The system includes a high precision and high input impedance analog front end, a high precision integrator, and a plurality of high input impedance and high gain difference amplifiers.

Having briefly described the present invention, the above and further objects, features and advantages thereof will be recognized by those skilled in the pertinent art from the following detailed description of the invention when taken in conjunction with the accompanying drawings.

DETAILED DESCRIPTION OF THE INVENTION

The present invention is a high-precision and high input impedance analog front end (either a standalone IC or constructed from a series of high input impedance operational amplifiers) cascaded with a high precision integrator and a pair of high input impedance and high (adjustable) gain difference amplifiers to construct a scalable linear-output potentiostat system with sensitivities below 1 nA (100 pA to 700 uA active range). This range can be adjusted via an external gain control. A high-resolution analog-to-digital converter is leveraged to obtain increased signal resolution to the femto- or atto-ampere level.

The high input impedance analog front end, paired with: an adjustable high precision integrator and a pair of mirrored difference amplifier or any variety of such; the use of the mirrored amplifiers and a subtraction algorithm allows the reduction of noise and the removal of fluctuations due to floating or drifting ground issues and external signal ingress; the combined system allows for the detection of extremely low currents without the use of off-board shielding elements (such as a faraday cage); a time average hardware filtering & sampling algorithm also aids in the stabilization of readings by eliminating interfering signal harmonics. A high-resolution analog-to-digital converter can also be leveraged to obtain increased signal resolution to the femto- or atto-ampere level, hence achieving near single-molecule sensitivity.

The elements of a preferred embodiment of the invention.

Figure 1:
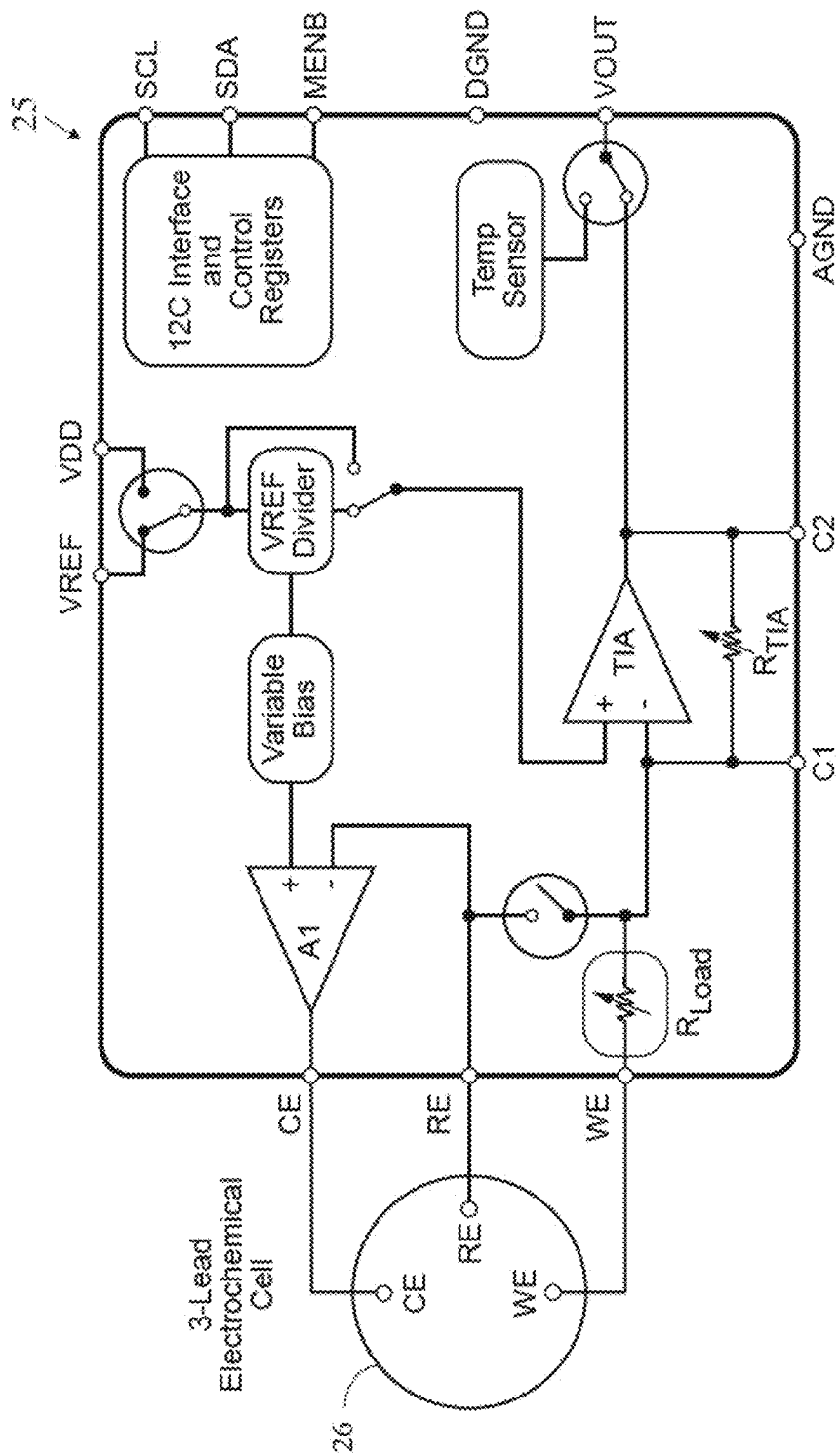
FIG. 1 is a circuit diagram of a standalone potentiostat integrated circuit.
Figure 2:
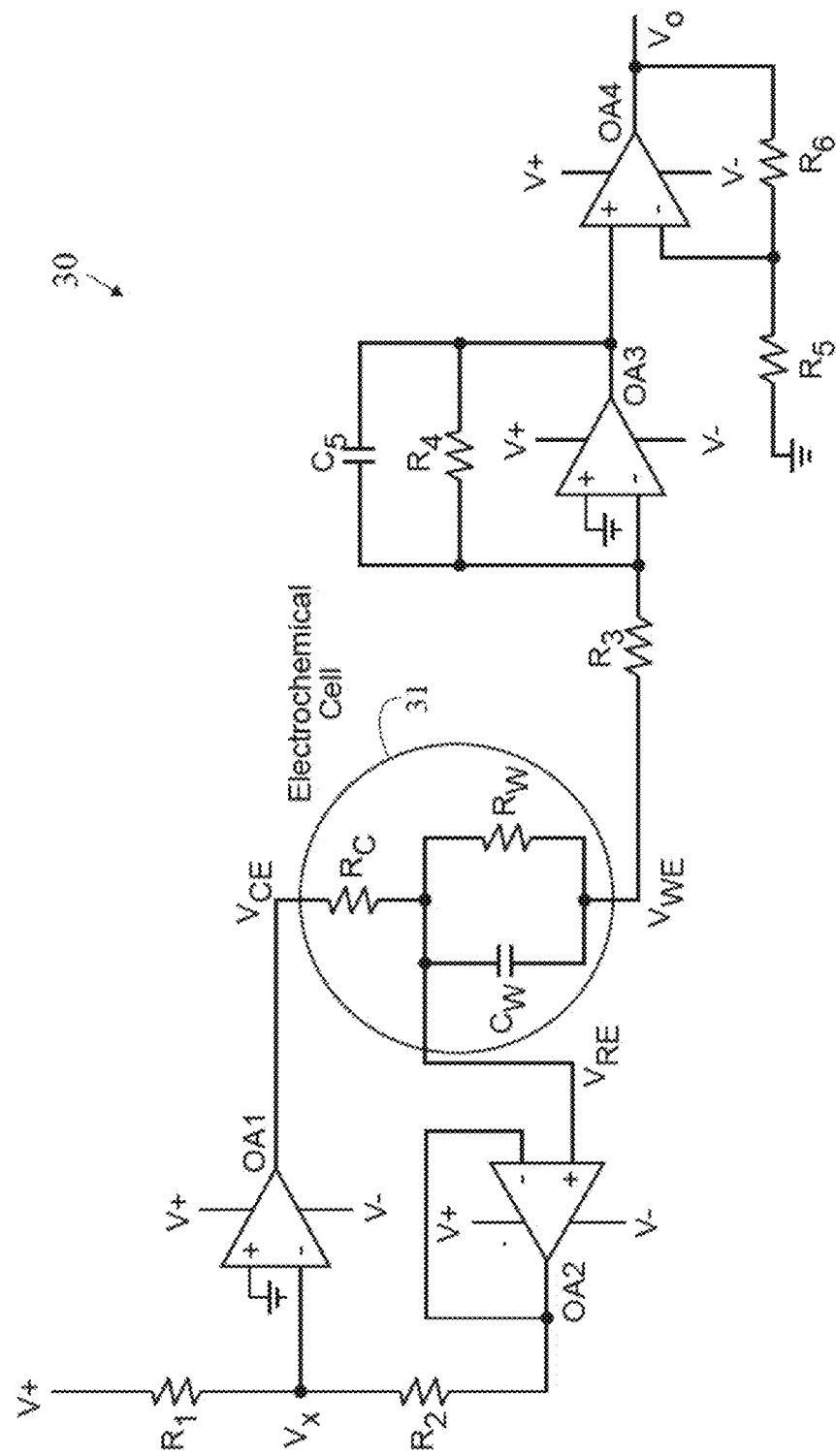
FIG. 2 is a circuit diagram of a multi-component potentiostat.

FIG. 1 is a circuit diagram of a standalone potentiostat integrated circuit 25. As shown in FIG. 1, an adjustable bias analog front end/potentiostat is composed of high-input impedance operational amplifiers and a digital to analog converter, or a standalone analog front end ("AFE") or analog interface integrated circuit package. FIG. 2 is a circuit diagram of a multi-component potentiostat 30.

An adjustable low noise transimpedance amplifier ("TIA") 42 converts current flow into a proportional voltage signal, which is adjustable through manual component selection or electronically controlled, and is configured for linear gain (TIA) or integration (integrator) via the implementation of a bypass capacitor.

A mirrored (inverted input) high input impedance and high (adjustable) gain difference amplifier is adjustable through physical resistors (a series of components—multiplexers, relays, and other signal paths—or a physically adjustable potentiometer) or electronically controlled resistors (digital potentiometers), and is configured as a base difference amplifier or any variety of such, including an instrumentation amplifier. Depending on the voltage polarity of the AFE and TIA combination, one amplifier will represent the signal and the second will represent any present ground interference or biases.

Signal filtering eliminates signal ripple due to electromagnetic interference ("EMI") following difference amplifier, and is implemented with active or passive low pass, high pass, band pass, or any combination thereof.

A high-resolution analog-to-digital converter is leveraged to convert the filtered analog signal to a precisely quantified value and used to obtain an increased signal resolution to the femto- or atto-ampere level.

A sampling algorithm involves time-average sampling plus offset. The opposing difference amplifier is used to subtract any ground offsets caused by EMI, removing the requirement for external shielding cages or true ground connections.

The method steps of the potentiostat operation are as follows:

The Analog Front End/Potentiostat Operation. The potentiostat/AFE unit consists of either two (FIG. 1) or three (FIG. 2) precision instrumentation operational amplifiers (A1/OA1, OA2, and TIA/OA3) configured in the following arrangement: control amplifier A1/OA1 amplifies the differential voltage ($V_x$ in FIG. 2) measured between a variable (programmable) bias and ground (with gain A) and supplies current through the counter electrode (CE). Upon sensing a voltage generated at the reference electrode (RE), A1/OA1 sinks sufficient current in order to maintain its output voltage at the input ($V_{RE}$) value. In turn, RE is adjusted and the output potential/current of A1/OA2 (a buffer or unity-gain amplifier) is modified accordingly. The control amplifier thus functions as a voltage-controlled current source that delivers sufficient current to maintain the reference electrode at constant potential and arbitrate the electrochemical reaction. In implementing negative feedback, it is imperative that A1/OA2 be able to swing to extreme potentials to allow full voltage compliance required for chemical synthesis. Furthermore, it is crucial that the OA2 possesses very high input impedance in order to draw negligible current; otherwise the reference electrode may deviate from its intended operating potential. In practice, the use of precision amplifiers possessing 20 fA (or lower) of input bias current enables unabated operation to the sub-picoampere level, which is suitable for nearly all electrochemical studies. The TIA/OA3 accepts the current sourced through the working electrode (WE) and outputs a voltage (converted by resistor/capacitor network $R_{TIA}/C_5+R_4$) proportional to the amount of current passing through electrode WE.

The Analog Front End and Applied Reference/Working Bias. In the system shown in FIGS. 1 and 2, the reference voltage ($V_{RE}$/RE) is held constant at the inverting and noninverting inputs for operational amplifier A1/OA2, respectively, while the working voltage is changed through a voltage divider, resistor network, or other means, to create an operational bias on the connected sensor. Current passing from CE to WE is directed into the noninverting input of a variable-gain transimpedance amplifier, which converts the current flow into a scaled voltage output (at C2 and/or VOUT/Vo) according to the relation $VOUT/Vo = -i_{cell} R_{4/TIA}$.

Figure 3:
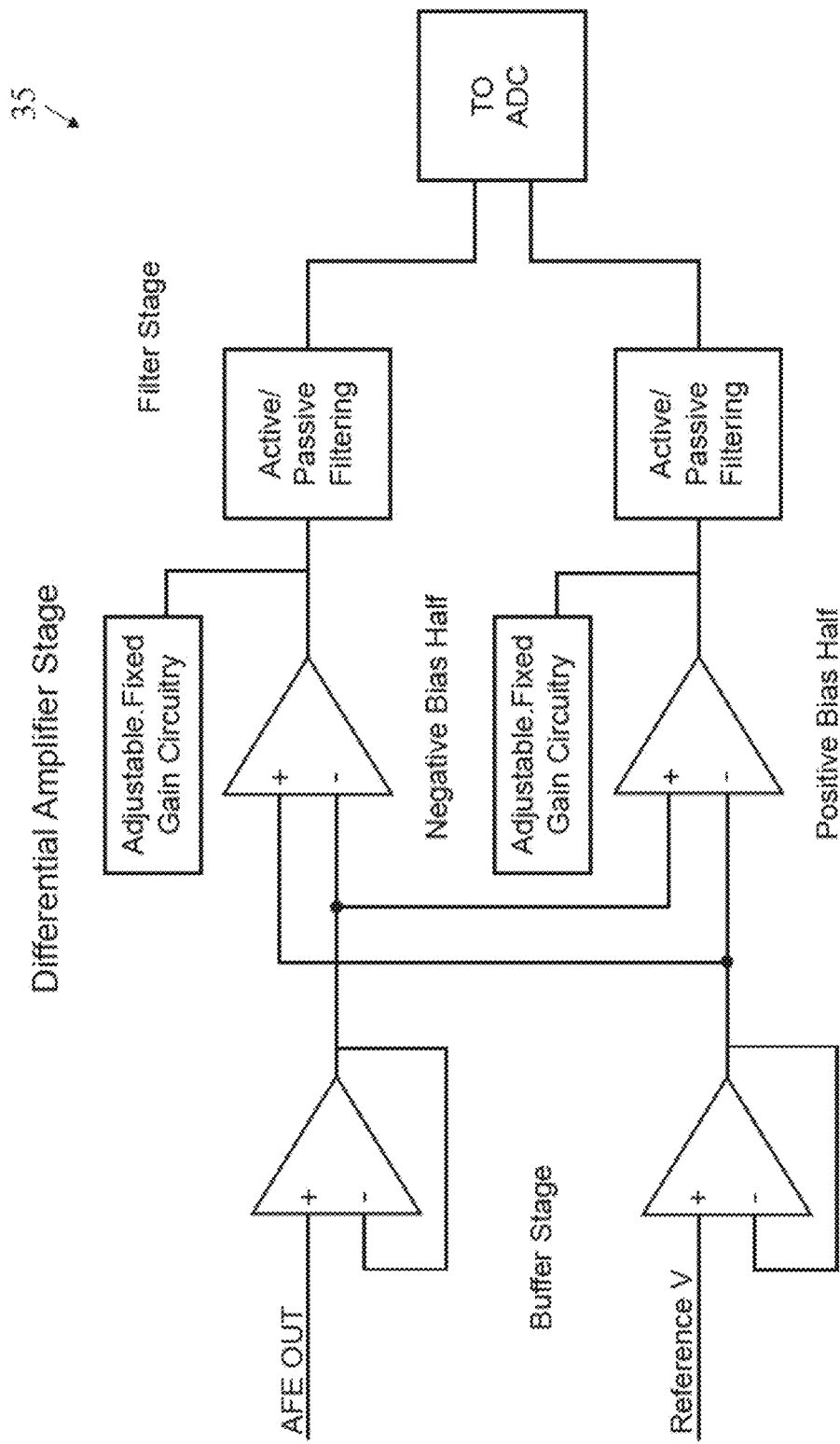
FIG. 3 is a block diagram of a difference amplifier.

The difference amplifier stage 35 is shown in FIG. 3. The difference amplifiers are configured to accept the applied reference voltage (RE or C1 in the internal IC diagram) and the output from the transimpedance amplifier (with or without a buffer stage). The inputs are juxtaposed among the two amplifiers, namely the reference input is connected to the positive terminal on one of the amplifiers (for negative applied voltages/currents) and on the negative terminal of the other (for positive applied voltages/currents). VOUT is connected to the opposing amplifier input. The unused amplifier (opposing the polarity of the applied current/voltage) will have its inputs driven to zero; it will, however, still possess a ground bias if one is present within the system. The gain of the difference amplifier can be configured either through manufacture or in real time to scale to the amount of voltage/current read in by the AFE.

The Filtering step. The outputs generated from the difference amplifier pair are subsequently subjected to a filtering circuit to remove extraneous noise. Oscillations or random fluctuations in the signal can be present due to a number of reasons, including ground bias, RF interference, mains power oscillation, input impedance mismatch (from the 3 electrode sensor), or from other sources.

The Analog to Digital Converter step. The filtered signals are lastly incident upon an analog to digital converter ("ADC"), either located in an external integrated circuit ("IC"), or co-located within a microcontroller or other IC, and converted into a representative digital signal. Increased sampling resolution may be implemented to gain additional sensitivity and minimize quantization error.

The Collection Algorithm step. To further reduce noise, a time averaged value for both positive and negative bias lines will be collected and computed by a microcontroller/microprocessor over a period of a few seconds (subsequent to digitization by the ADC). The active bias amplifier (applied voltage/current) will have the value of the inactive bias amplifier (ground offset) subtracted in order to remove any present bias in the device. Due to this process, a shielding cage is not required to reach picoampere levels of sensitivity. The inactive bias amplifier, time average data collection, and filtering schemes will provide a stable and scalable output into the microcontroller/processor at all times.

Inputs and outputs of the invention.

The input of the electrochemical cell or sensor, the analyte, is measured by controlled-potential techniques (amperometry, voltammetry, etc). The output of the sensing system, consisting of a measured voltage and calculated current value (determination of current flowing through working and counter electrodes of electrochemical cell or sensor), corresponds to the concentration of the analyte in the sample.

Figure 4:
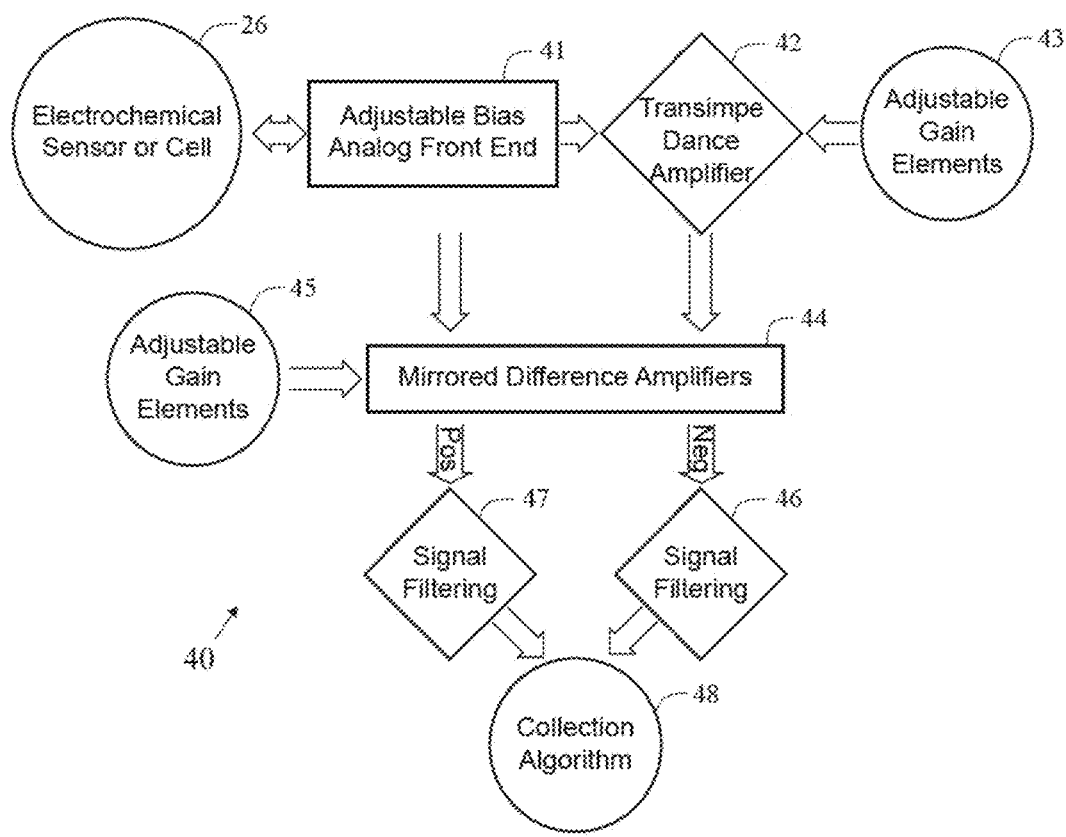
FIG. 4 is a signal flow diagram of the present invention.

FIG. 4 illustrates a signal flow diagram 40 for detecting a current flowing an electrochemical cell. A current signal from an electrochemical cell 26 is sent to an adjustable bias analog front end 41. The signal is sent to a transimpedance amplifier 42 as are adjustable gain elements 43. The signal is sent from both the adjustable bias analog front end 41 and the transimpedance amplifier 42 to mirrored difference amplifiers 44 as are adjustable gain elements 45. The outputs generated from the mirrored difference amplifiers 44 are subsequently subjected to filtering circuits 46 and 47 to remove extraneous noise. Oscillations or random fluctuations in the signal can be present due to a number of reasons, including ground bias, RF interference, mains power oscillation, input impedance mismatch (from the 3 electrode sensor), or from other sources. At the collection algorithm 48, to further reduce noise, a time averaged value for both positive and negative bias lines is collected and computed by a microcontroller/microprocessor over a suitable time period, such as a few seconds (subsequent to digitization by the ADC). The active bias amplifier (applied voltage/current) will have the value of the inactive bias amplifier (ground offset) subtracted in order to remove any present bias in the device. Due to this process, a shielding cage is not required to reach picoampere levels of sensitivity. The inactive bias amplifier, time average data collection, and filtering schemes will provide a stable and scalable output into the microcontroller/processor/ADC at all times.

Figure 5:
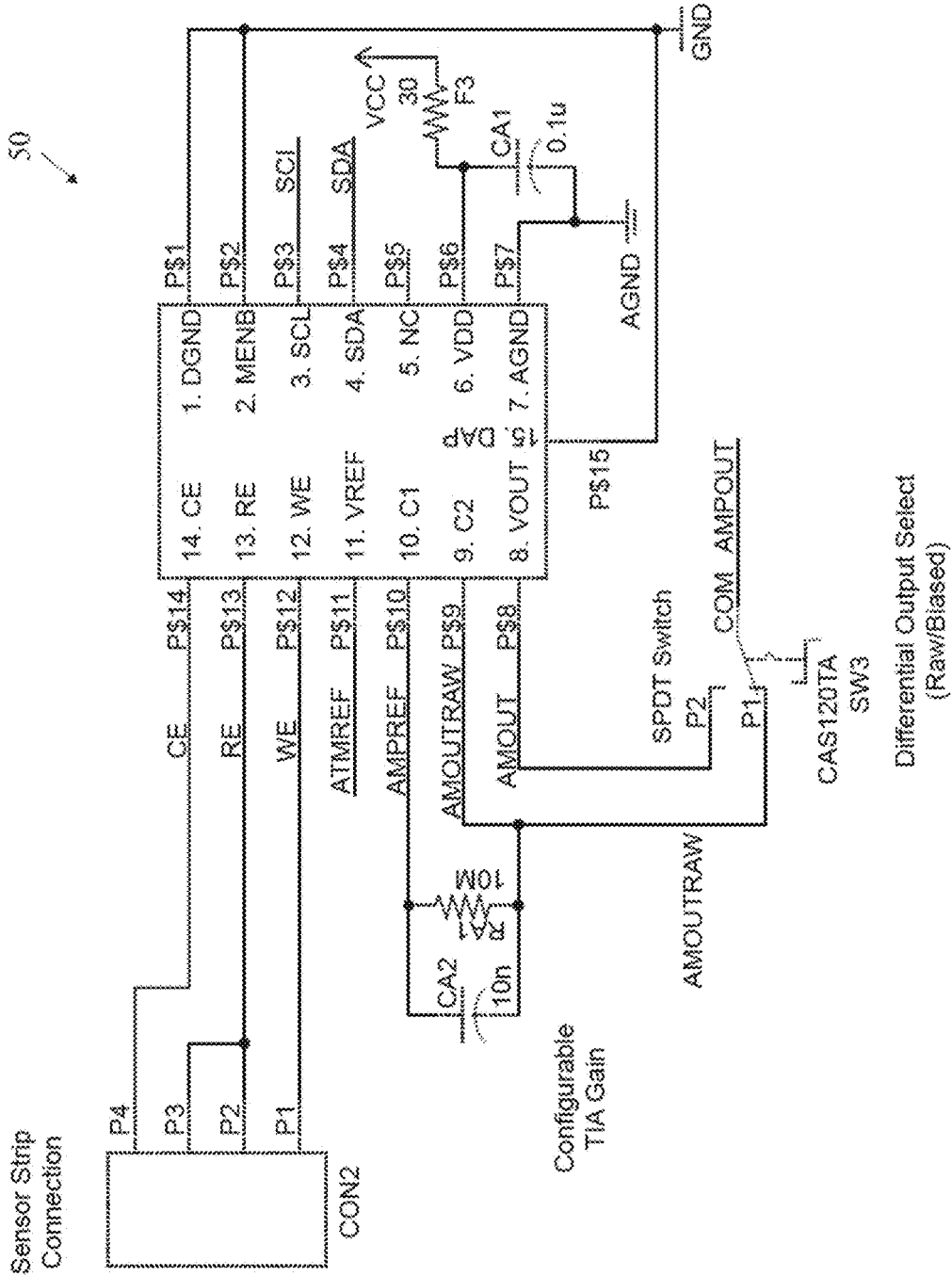
FIG. 5 is a circuit diagram of an integrated analog front end and sensor interface.

FIG. 5 is a detailed circuit diagram of an integrated analog front end 50 and sensor interface. This is a circuit diagram of an integrated AFE available from a manufacturer that communicates (SCL and SDA lines) with a central microcontroller/microprocessor unit and controls an electrochemical sensor via the CE (counter electrode), WE (working electrode), and RE (reference electrode) lines. The configurable circuit components for the transimpedance amplifier (TIA) are present across 9 and 10 and forms an integrator as configured in the image.

Figure 6:
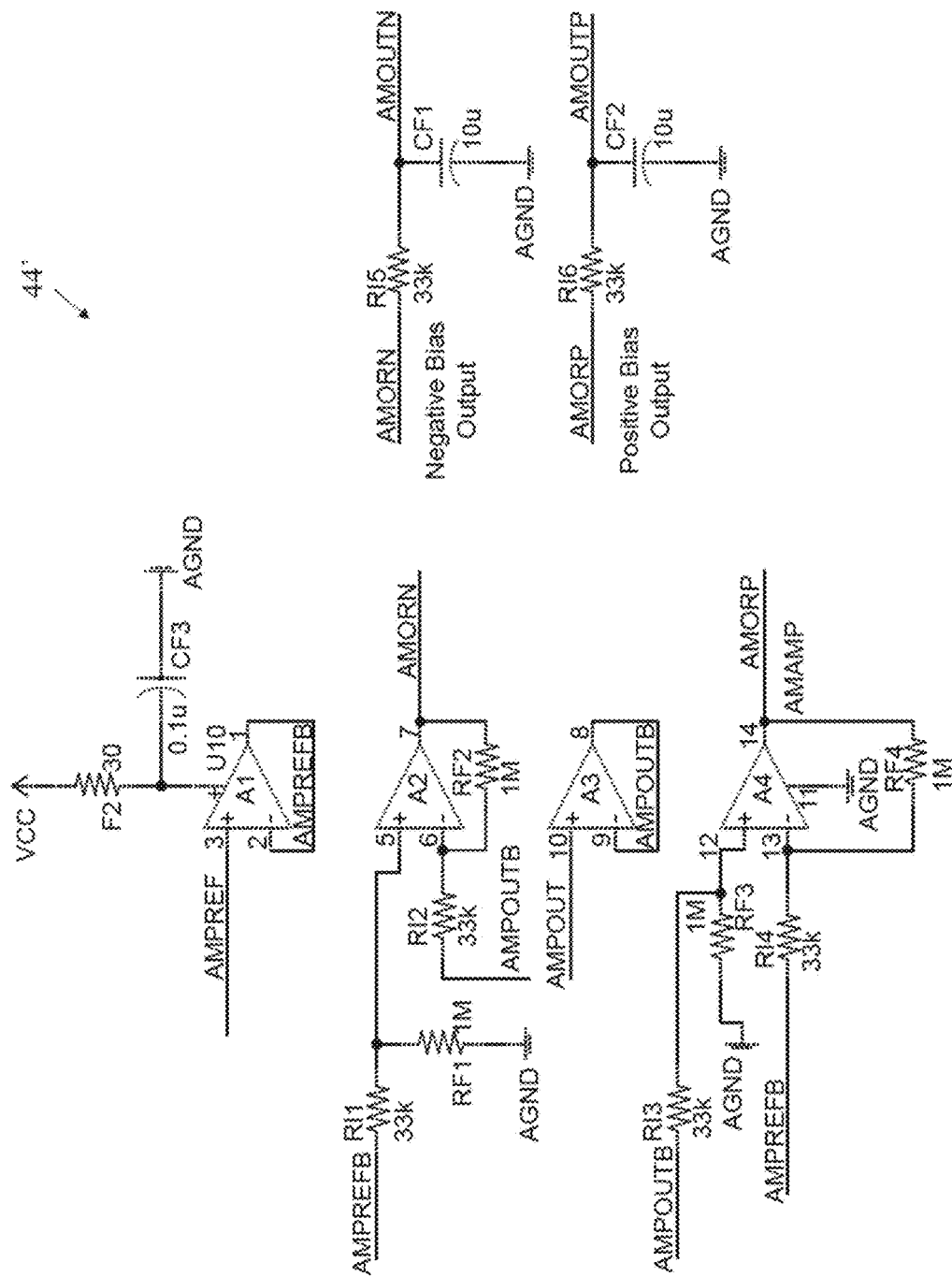
FIG. 6 is a circuit diagram of mirrored difference amplifiers and filtering.

FIG. 6 is a detailed circuit diagram of mirrored difference amplifiers 44' and filtering. Here, a set of mirrored difference amplifiers is shown utilizing individual operational amplifier components (left side) and a low pass filter on the output (right side). AMORP and AMORN are the positive and negative differential signals, and AMOUTN and AMOUTP are the filtered differential signals. Output gain is controlled by the passive resistors connected to the amplifiers.

Figure 7:
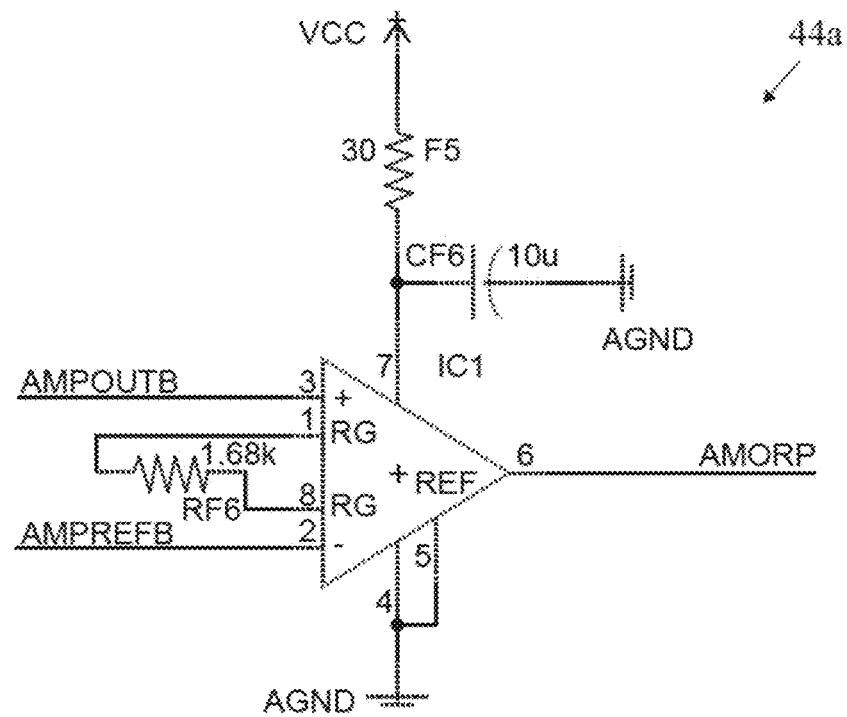
FIG. 7 is a circuit diagram of fixed mirrored instrumentation amplifiers.
Figure 7:
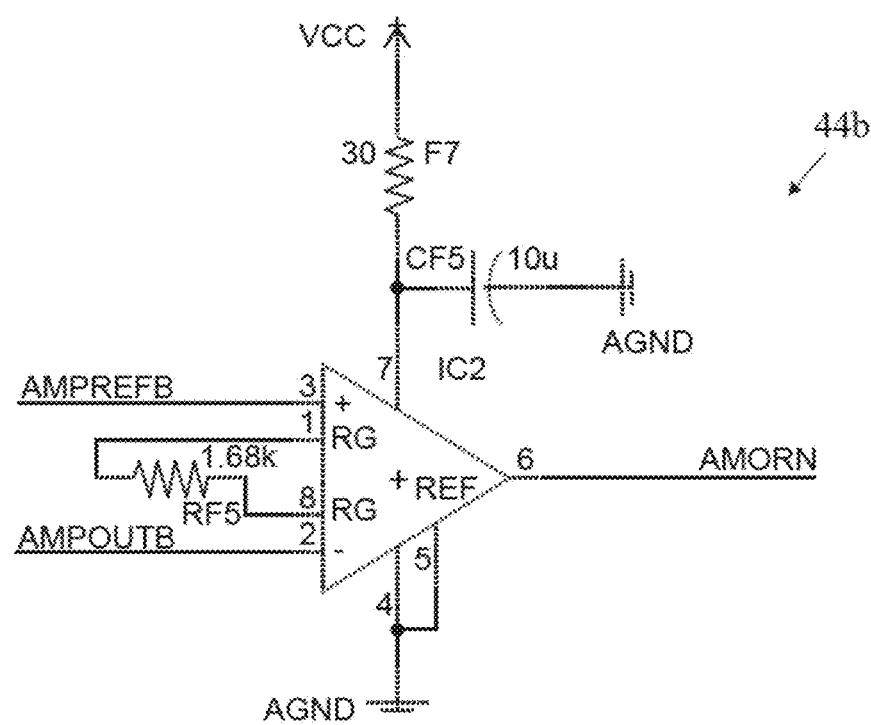

FIG. 7 is a detailed circuit diagram of fixed mirrored instrumentation amplifiers 44a and 44b. Here, a set of mirrored difference amplifiers is shown using a pair of integrated instrumentation amplifiers. Output gain is controlled by a single resistor connected to the RG terminals.

Figure 8:
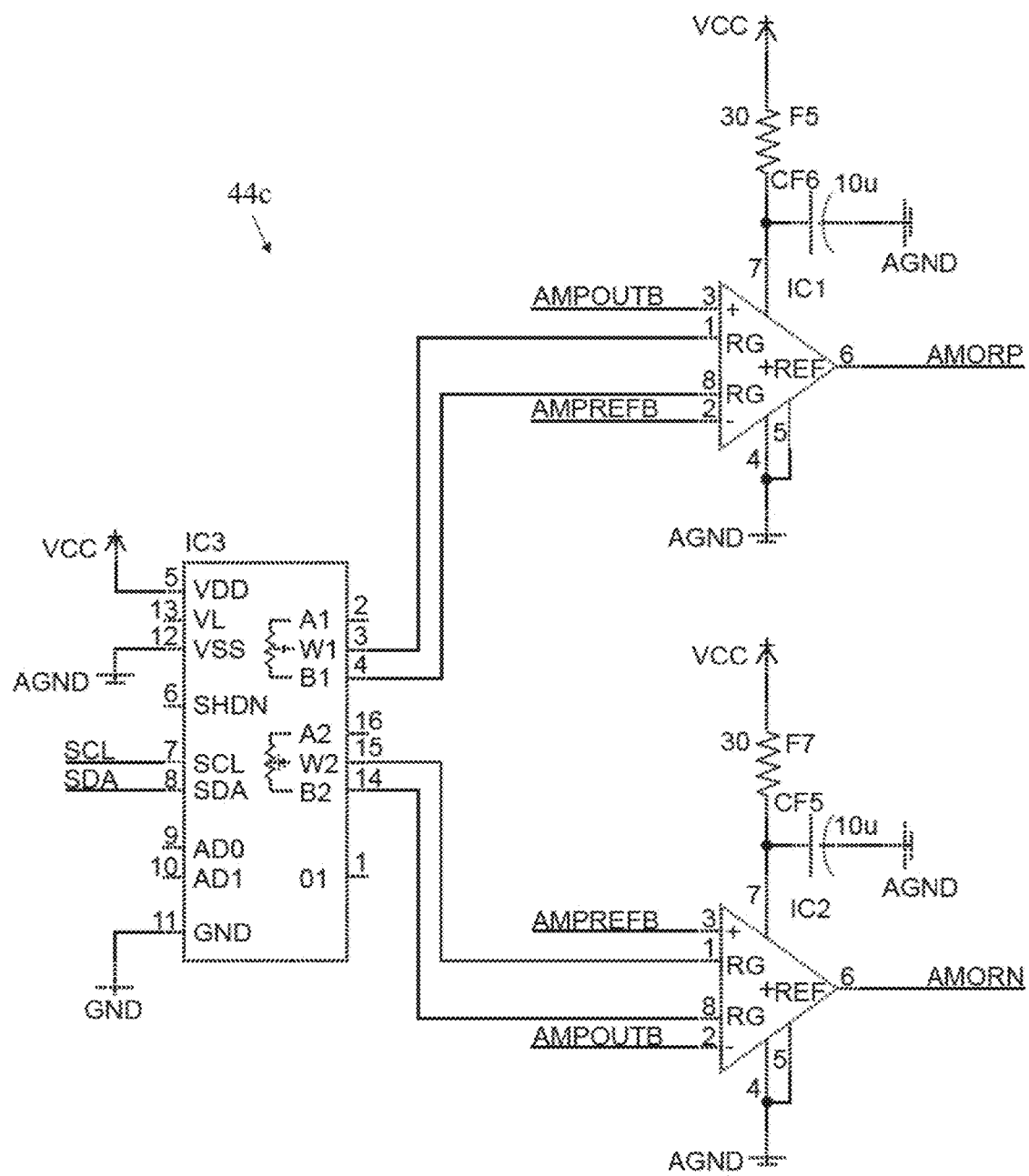
FIG. 8 is a circuit diagram of digital potentiometer-adjustable mirrored instrumentation amplifiers.

FIG. 8 is a detailed circuit diagram of digital potentiometer-adjustable mirrored instrumentation amplifiers 44c. This is similar to FIG. 7, albeit utilizing a programmable/digitally selectable gain resistor integrated circuit (IC3) rather than passive components.

Figure 9:
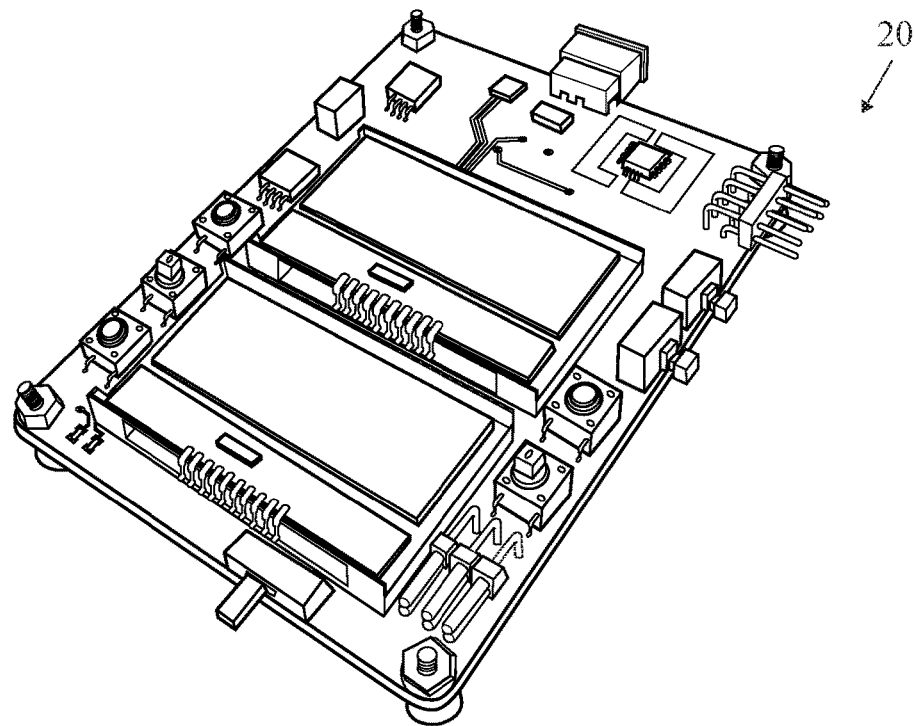
FIG. 9 is an illustration of a handheld analyzer in a large form factor.

FIG. 9 is an illustration of a handheld analyzer 20 in a large form factor.

Figure 10:
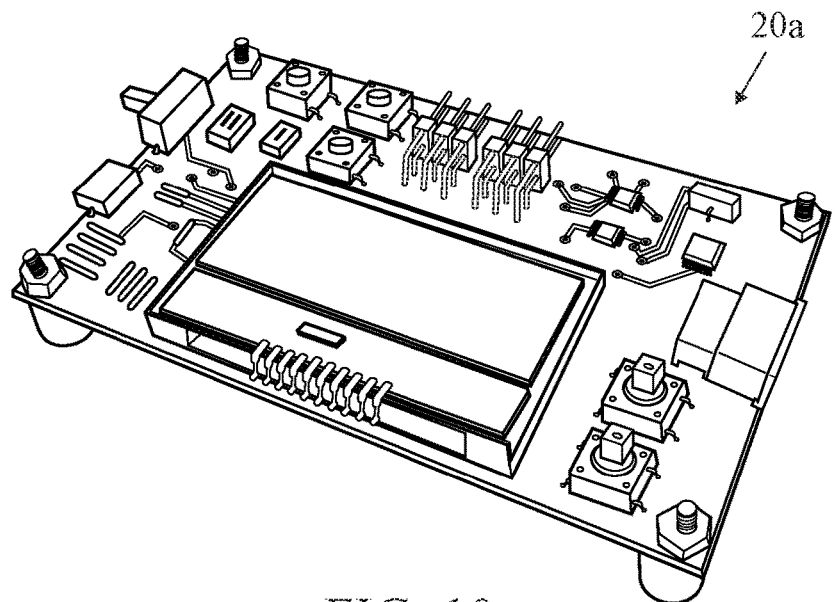
FIG. 10 is an illustration of a handheld analyzer in a small form factor.

FIG. 10 is an illustration of a handheld analyzer 20a in a small form factor.

Figure 12:
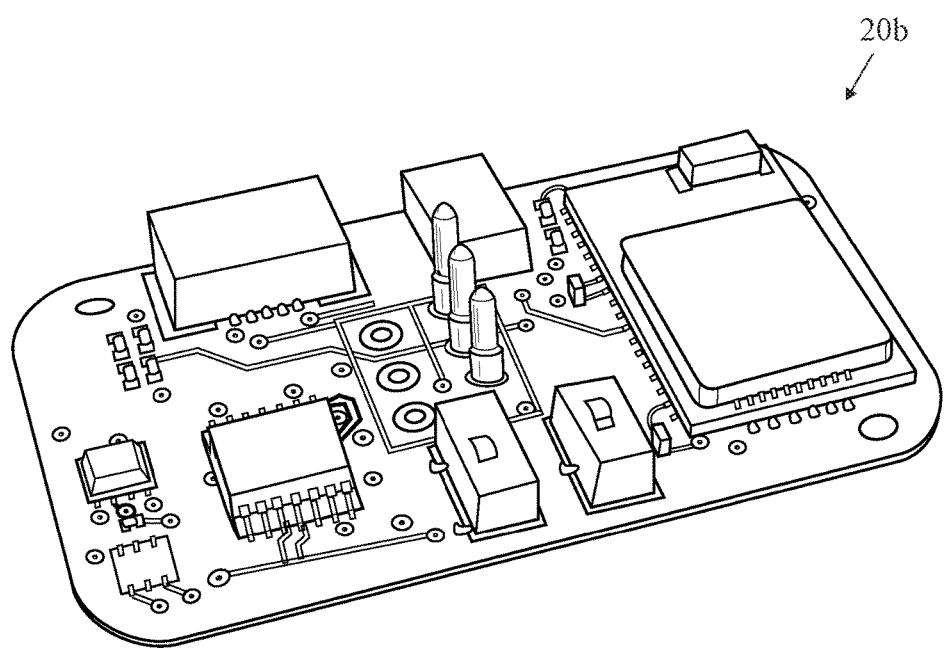
FIG. 12 is an illustration of a handheld analyzer in a small form factor.

FIG. 12 is an illustration of a handheld analyzer 20b in a small form factor.

Figure 11:
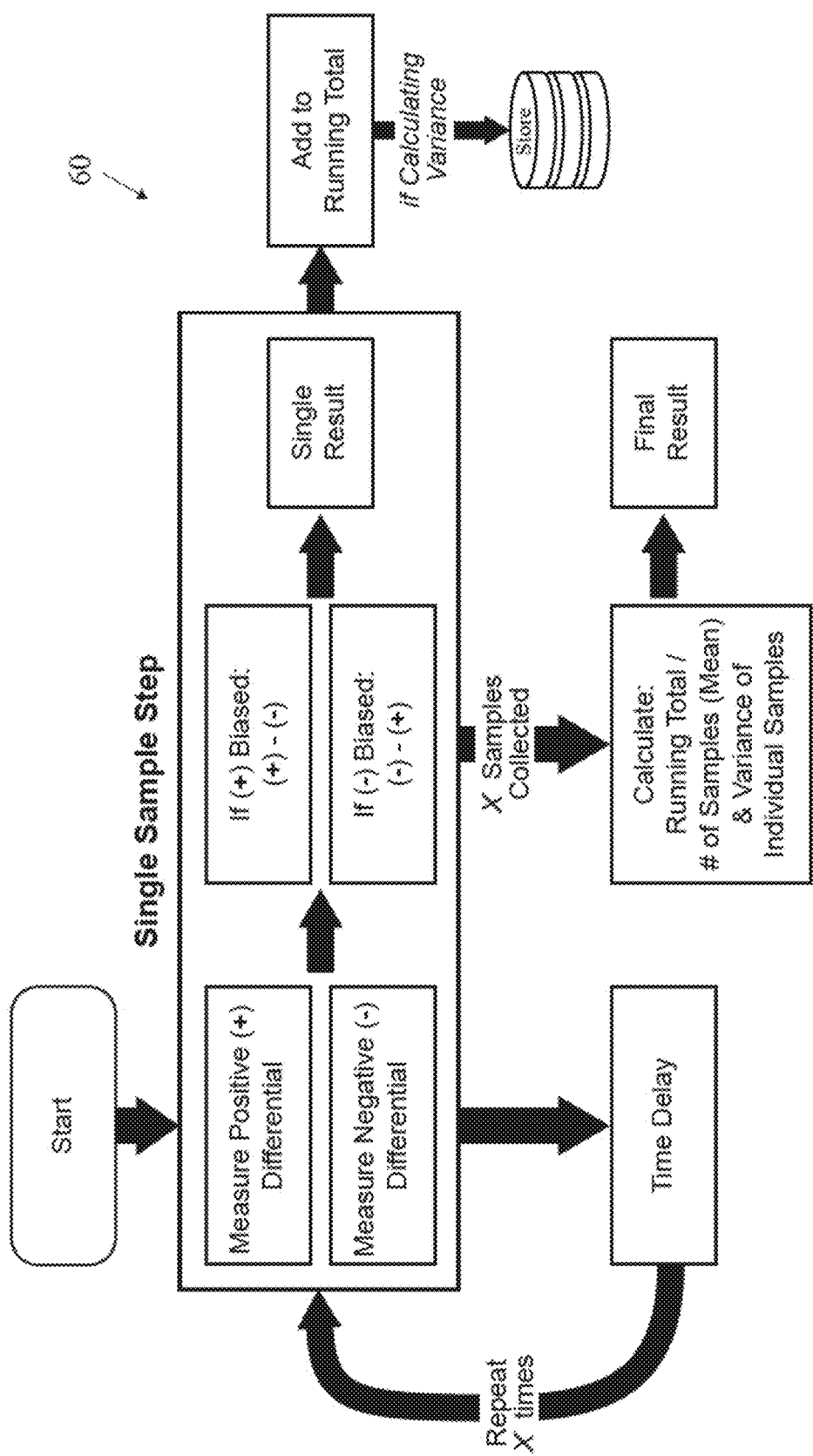
FIG. 11 is a block diagram of a sample algorithm.

The sampling and measurement algorithm is designed to minimize sources of noise that are not compensated or otherwise removed using the circuit hardware. As shown in the block diagram 60 of FIG. 11, each "sample" involves reading both the positive and negative differential outputs and subtracting one from the other. Multiple samples can be collected and analyzed via statistical operations to yield a measurement. The simplest form is to calculate mean and variance/standard deviation from a set of individual samples. The sampling period has to be selected in a manner that minimizes the possibility of noise from other electrical sources.

The main sources of noise are: floating ground and ground drift; mains power; and high frequency interference.

The floating ground and ground drift are compensated by various means. Floating ground (DC noise) is compensated by the presence of the paired difference amplifiers. Ground drift is compensated by averaging multiple samples. If measuring a positive bias/current, the negative output will be equal to the floating ground. Subtracting the negative output from the positive will remove noise caused by ground drift. The opposite can be performed when measuring a negative bias/current. The subtraction step should be performed at each sample rather than using averages of multiple readings.

Mains Power is also compensated in various ways. Noise arising due to mains power when either connected to an AC power line or induced by proximity to other AC line-powered equipment is compensated by selection of the algorithm sampling period. Sampling should never be performed at the same delay as the period of the line power cycle (16 or 20 ms for 60 Hz and 50 Hz power systems, respectively) or any multiple thereof (i.e. 32 to 40 ms for a multiple of two, etc). If sampling delay is less than the line power cycle (16-20 ms), at least one cycle (at 50-60 Hz) must be captured by multiple samples. For proper statistical analysis, enough samples must be collected to establish an adequate estimate of the standard deviation and mitigate power line harmonics. For a 95% confidence interval for Type 1 (false positive) and Type 2 (false negative) errors, for example, at least 13 samples must be measured. This is application-specific but a minimum of 10 samples is recommended. The maximum sample number is application-dependent (the likelihood of sudden changes due to external factors, such as movement in the case of a body worn sensor).

High frequency interference, noise due to wireless transmission and other high frequency signals, is eliminated fully by hardware filtering, notably low pass filtering.

From the foregoing it is believed that those skilled in the pertinent art will recognize the meritorious advancement of this invention and will readily understand that while the present invention has been described in association with a preferred embodiment thereof, and other embodiments illustrated in the accompanying drawings, numerous changes modification and substitutions of equivalents may be made therein without departing from the spirit and scope of this invention which is intended to be unlimited by the foregoing except as may appear in the following appended claim. Therefore, the embodiments of the invention in which an exclusive property or privilege is claimed are defined in the following appended claims.

We claim as our invention the following:

1. An analyzer for the detection of low concentrations of analytes, the analyzer comprising:
   an adjustable bias analog front end comprising a plurality of high-input impedance operational amplifiers and a digital-to-analog converter;
   an adjustable low noise transimpedance amplifier;
   a mirrored high input impedance and high gain difference amplifier;
   a processor;
   a filtering circuit configured to filter a signal;
   a high-resolution analog-to-digital converter; and
   a sampling algorithm.

2. The analyzer according claim 1 wherein the processor is configured to run a subtraction algorithm for reduction of noise and removal of fluctuations in the signal.

3. The analyzer according to claim 1 wherein the analyzer does not include an off-board shielding element.

4. The analyzer according to claim 1 further comprising an analog-to-digital converter.

5. The analyzer according to claim 1 wherein the processor is configured to run a time average hardware filtering and a sampling algorithm to stabilize a plurality of readings and to eliminate a plurality of interfering signal harmonics.

6. The analyzer according to claim 1 wherein the processor is configured to run a collection algorithm.

7. The analyzer according to claim 1 wherein the analyzer is sensitive to detection of a current within a range of 1 pico Amperes to 700 micro Amperes.

8. The analyzer according to claim 1 wherein the filtering circuit comprises a combination of at least one of a high pass filter, a band pass filter, a passive low pass filter, and an active filter.

9. The analyzer according to claim 1 wherein the analyzer is for at least one of detection of extremely low currents, potentiometry, coulometry, polarography, conductometry, impedimetry, amperometry and voltammetry.

* * * * *